United States Patent [19]

Ikeda

[11] Patent Number: 5,104,413
[45] Date of Patent: Apr. 14, 1992

[54] HAIR DYE COMPOSITION

[75] Inventor: Yoshio Ikeda, Ichikawa, Japan

[73] Assignee: Kao Corporation, Tokyo, Japan

[21] Appl. No.: 581,791

[22] Filed: Sep. 13, 1990

[30] Foreign Application Priority Data

Oct. 24, 1989 [JP] Japan .................. 1-276612

[51] Int. Cl.⁵ .............................. A61K 7/13
[52] U.S. Cl. ......................... 8/405; 8/406; 8/407; 8/408; 8/428; 8/429; 8/431; 8/432; 8/435
[58] Field of Search .................. 8/405, 407, 408, 428, 8/429, 435, 406, 431, 432

[56] References Cited

U.S. PATENT DOCUMENTS 4,746,322  5/1988  Herlihy .................................. 8/406
4,935,032  6/1990  Grollier ................................. 8/428

FOREIGN PATENT DOCUMENTS 3104739  9/1978  Japan .
3104741  9/1978  Japan .
2-178216  7/1990  Japan .

*Primary Examiner*—A. Lionel Clingman
*Assistant Examiner*—William S. Parks
*Attorney, Agent, or Firm*—Birch, Stewart, Kolasch & Birch

[57] ABSTRACT

A hair dye composition comprising the following three components (A), (B) and (C):

(A) one or more cysteine derivatives selected from among a compound represented by the following general formula (I):

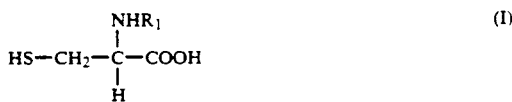

wherein $R_1$ represents a hydrogen atom or an acyl or alkyl group carrying one to three carbon atoms, and glutathione, or a salt thereof;

(B) an aromatic alcohol and/or a compound represented by the following general formula (II):

$$R_2\text{-OCH}_2\text{CH}_2\text{OCH}_2\text{CH}_2\text{OH} \qquad (II)$$

wherein $R_2$ represents an alkyl group carrying one to five carbon atoms; and (C) a dye.

10 Claims, No Drawings

HAIR DYE COMPOSITION

BACKGROUND OF THE INVENTION

1. Field of the Invention

This invention relates to a hair dye composition capable of dyeing the hair by applying it to the hair.

2. Description of the Prior Art

Most of known hair dyes comprise oxidation dyes such as p-phenylenediamine, p-aminophenol or resorcinol as an active ingredient. It is indispensable to use an oxidizing agent in using such a conventional oxidation hair dye. Thus these hair dyes contain peroxides such as hydrogen peroxide or perborates. Furthermore, conventional oxidation hair dyes contain basic compounds such as ammonia or monoethanolamine in order to promote swelling of the hair and decomposition of the peroxides.

However the above-mentioned oxidizing agents and basic compounds suffer from some troubles that they would irritate the skin, eyes or scalp and that they would make the hair brittle because they cleave chemical bonds of cystine as a constituent of the hair so as to give damage to the hair.

Therefore Japanese Patent Laid-Open No. 104739/1978 and No. 104741/1978 proposed to dye the hair with the use of a cysteine derivative together with a dye.

However each of these attempts gives unsatisfactory "dyeing properties" and "shampoo-fastness".

On the other hand, so-called temporary dyes comprising direct dyes (nonpolymeric dyes) such as acid dyes or basic dyes are mild to the hair and skin. However, consumers are not satisfied with these dyes, since they show insufficient dyeing properties or suffer from considerable decoloring once shampooed.

SUMMARY OF THE INVENTION

It is an object of the present invention to provide a hair dye composition which is excellent in dyeing properties and shampoo-fastness, scarcely irritates the skin and relieves damage to the hair.

In order to solve the above-mentioned problems, the present inventors have conducted extensive studies. As a result, they have found out that a hair dye composition essentially comprising a specific cysteine derivative, an aromatic alcohol and/or diethylene glycol monoalkyl ether and a dye shows extremely improved "dyeing properties" and "shampoo-fastness", thus achieving the above-mentioned object.

The present invention, which has been completed based on the above finding, provides a hair dye composition comprising the following three components (A), (B) and (C):

(A) one or more cysteine derivatives selected from among a compound represented by the following general formula (I):

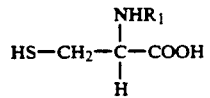
(I)

wherein $R_1$ represents a hydrogen atom or an acyl or alkyl group carrying one to three carbon atoms; and glutathione, or a salt thereof;

(B) an aromatic alcohol and/or a compound represented by the following general formula (II):

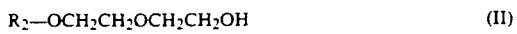

wherein $R_2$ represents an alkyl group carrying one to five carbon atoms; and (C) a dye.

The hair dye composition of the present invention, which is excellent in dyeing properties and shampoo-fastness, makes it possible to uniformly and deeply dye the hair. It is particularly advantageous in its extremely high shampoo-fastness, compared with conventional ones (temporary hair dyes). Furthermore, the hair dye composition of the present invention scarcely irritates the skin and prevents damage to the hair.

DETAILED DESCRIPTION OF THE INVENTION

Examples of the cysteine derivative or a salt thereof to be used as the component (A) in the hair dye composition of the present invention include N-acetyl-3-mercaptoalanine (hereinafter called N-acetylcysteine), N-propyl-3-mercaptoalanine, N-ethyl-3-mercaptoalanine and glutathione. Either one of these cysteine derivatives or their salts or a mixture thereof may be used. The content of the component (A) in the hair dye composition of the present invention may preferably range from 0.05 to 5.0% (by weight, the same will apply hereinafter), in particular, from 0.1 to 3.0%.

Examples of the salt of the cysteine derivative as the component (A) include inorganic acid salts such as hydrochloride, sulfate and nitrate and organic acid salts such as acetate, formate, oxalate and citrate. Among these salts, hydrochloride is preferable in particular.

As the aromatic alcohol of the component (B) of the hair dye composition of the present invention, a phenyl monoalkyl alcohol represented by the following general formula (III):

wherein h is a number of from 1 to 5, is preferable. A compound of the general formula (III) wherein h is 1 is particularly preferable. The content of the aromatic alcohol in the hair dye composition of the present invention may preferably range from 0.1 to 50%, particularly from 0.1 to 20%.

Examples of the diethylene glycol monoalkyl ether represented by the general formula (II) as the component (B) of the hair dye composition of the present invention include diethylene glycol methyl ether, diethylene glycol ethyl ether, diethylene diglycol propyl ether, diethylene glycol butyl ether and diethylene glycol pentyl ether. Among these compounds, diethylene glycol ethyl ether, diethylene glycol propyl ether and diethylene glycol butyl ether are preferable. The content of these diethylene glycol alkyl ethers may preferably range from 0.1 to 50%, in particular, from 0.1 to 30%.

In the present invention, either one of the diethylene glycol alkyl ether and the aromatic alcohol or both of them may be used as the component (B).

The dye to be used as the component (C) in the hair dye composition of the present invention is not particularly restricted. A direct dye or a natural coloring matter is preferable therefor.

Examples of the direct dye include all of nonpolymeric dyes such as nitrogenous benzene derivatives, indoamine dye, diaryl and xanthene, triarylmethane dye, azine, acridine and anthraquinone dyes.

These dyes may have nonionic, acidic or basic substituents. Particular examples thereof are as follows:

Red No. 3 (C.I. 45430), Blue No. 2 (C.I. 73015), Black No. 401 (C.I. 20470), Purple No. 401 (C.I. 60730), Green No. 401 (C.I. 10020), Yellow No. 405 (C.I. 11390), Basic Brown 17 (C.I. 12251), Basic Brown 16 (C.I. 12550), Basic Red 76 (C.I. 12245), Basic Blue 99 (C.I. 56059) and Basic Yellow 57 (C.I. 12719).

Examples of the natural coloring matter include henna, German chamomile, corn flower and walnut.

The content of these dyes in the hair dye composition of the present invention may preferably range from 0.0001 to 20%, in particular, from 0.001 to 5%. Either one of the above-mentioned dyes or a mixture thereof may be used.

In addition to the above-mentioned essential components, the hair dye composition of the present invention preferably contains one or more inorganic or organic alkaline agents so as to adjust the pH value of the hair dye composition to 6 to 10, still preferably 7 to 9. It is furthermore preferable to use buffers.

Examples of the buffers include the following combinations: citric acid/disodium hydrogenphosphate, hydrochloric acid/barbital sodium/sodium acetate, hydrochloric or maleic acid/trishydroxyaminomethane, potassium or sodium dihydrogenphosphate/dipotassium or sodium hydrogenphosphate, hydrochloric acid or potassium or sodium dihydrogenphosphate/sodium tetraborate, potassium or sodium dihydrogenphosphate/sodium or potassium hydroxide, hydrochloric acid/collidine, boric acid/sodium carbonate or tetraborate, hydrochloric acid/aminomethylpropanediol, glycine/sodium or potassium hydroxide, boric acid/sodium hydroxide, hydrochloric acid/dimethylglycine sodium, sodium hydrogencabonate/sodium carbonate, sodium tetraborate/sodium hydroxide, sodium hydrogencarbonate/sodium hydroxide and water-soluble ammonium salt/ammonia. Among them, those which give little alkaline agents remaining on the hair and scarcely give damage to the hair or irritate the skin (for example, ammonium bicarbonate, ammonium carbonate, ammonia, glycine, arginine or lysine) are preferable. Either one of these buffers or a mixture thereof may be used.

Furthermore, the hair dye composition of the present invention may contain other conventional components, so long as the effects of the present invention are not deteriorated thereby. Examples of these additional components include higher alcohols, cationic, anionic and amphoteric surfactants, urea, silicone, aluminum compounds such as aluminum stearate and alum, organic acids such as citric acid and malic acid, inorganic acids such as hydrochloric acid, ethylenediamine, mono-, di- and triethanolamines, morpholine, basic amino acids such as arginine and lysine, alkaline agents such as ammonia and caustic soda, hair nourishments, bactericides, colorants and perfumes.

The hair dye composition of the present invention may be formulated into various forms, namely, not only common liquid or cream hair dye but also dyeing and styling composition containing a styling component such as styling mousse and gel.

The method for the application of the hair dye composition of the present invention is not particularly restricted. For example, it may be applied to the hair and then allowed to stand as such for a given period. Then the above-mentioned composition adhering to the hair is washed away with water. Alternately, the dyeing and styling composition may be directly applied to the hair.

The "dyeing properties" and "shampoo-fastness" of the hair dye composition can be further improved by heating in its application. The heating may be effected by using, for example, a steamer, an infrared lamp or a far-infrared lamp commonly employed therefor.

The above-mentioned hair dye composition may be used in an amount of from 10 to 150 ml for every application, though it varies depending on various factors including the heating temperature.

Next, the hair is heated to 40° to 160° C. The heating temperature and period would vary depending on the extent of damage to the hair, the employed buffer, pH and the form of the hair dye composition. In the case of normal hair which has been neither dyed nor bleached, a higher temperature is more advantageous. However it is preferable to conduct the heating at 40° to 160° C., in particular 40° to 80° C., so as to inhibit the thermal damage to the hair. It is further effective to cover the hair with a cap to thereby prevent the moisture of the hair from evaporating and to further moisten the hair during the heating. Alternately, it is also effective to conduct the heating while moistening the hair with, for example, a steamer. The time required for the heating would be prolonged with a lowering in the temperature. However, it is preferable to complete the heating within 30 minutes, still preferably from 3 to 20 minutes, from the same viewpoint as the one described above. In the case of chemically treated hair (for example, permed, dyed or bleached hair), it is preferable to select more mild conditions.

To further illustrate the present invention, and not by way of limitation, the following Examples will be given.

EXAMPLE 1

Hair dye compositions of the formulation as specified in Table 1 were prepared. Then the "dyeing properties" and "shampoo-fastness" of each of the compositions were evaluated based on the following criteria.

(1) Test on dyeing properties

Approximately 2 g of a test solution was uniformly applied to a goat hair bundle (white, approximately 1 g) with a brush. Then the excessive test solution was removed so as to adjust the weight of the hair bundle to 2 g (bathing ratio: 1:1). After maintaining in a thermostat (30° C.) for 15 minutes, the hair bundle was rinsed with running water at 40° C. for 30 seconds and dried. Then the dyeing properties were evaluated with the naked eye. Four hair bundles were employed for each test solution.

Criteria of evaluation

⊚: excellent dyeing (uniformly and deeply dyed without showing the white base color of the goat hair).
○: good dyeing (uniformly and deeply dyed).
Δ: insufficient dyeing (showing unevenness and faintly dyed in general).
×: poor dyeing.
(2) Test on shampoo-fastness Two hair bundles, among four ones obtained in the above test on dyeing properties, were rinsed with running water at 40° C. for 30 seconds. Then approximately 1 g of a shampoo solution (0.15% aqueous solution of polyoxyethylene lauryl ether sulfate sodium 2.5 E.O) was applied to each bundle. After washing by rubbing with hands for 30 seconds, the bundle was rinsed with running water at 40° C. for 30 seconds. This procedure was repeated 10 times. After the first, third, eighth and tenth runs, the bundle was dried to evaluate the extent of decoloring (i.e., shampoo-fastness) with the naked eye. The evaluation was conducted by comparing the two remaining bundles obtained in the above test on dyeing properties (standard dyed hair bundles).

Criteria of evaluation

⊙: the same as the standard dyed hair bundles.
○: almost the same as the standard dyed hair bundles.
Δ: obvious decoloring compared with the standard dyed hair bundles.
X: serious decoloring (scarcely dyed).

| Formulation (%) | | Control 1 | Invention 1 | Invention 2 | Invention 3 | Invention 4 | Control 2 |
|---|---|---|---|---|---|---|---|
| N-acetylcysteine | | 0.2 | 0.2 | 0.2 | 0.2 | 0.2 | common temporary dye |
| diethylene glycol eithyl ether | | — | 5.0 | — | 5.0 | 5.0 | |
| benzyl alcohol | | — | — | 5.0 | 5.0 | 5.0 | |
| ethanol (95%) | | 10.0 | 10.0 | 10.0 | 10.0 | 10.0 | |
| propylene glycol | | 10.0 | 10.0 | 10.0 | 10.0 | 10.0 | |
| Purple No. 401 | | 0.1 | 0.1 | 0.1 | 0.1 | 0.1 | |
| Black No. 401 | | 0.1 | 0.1 | 0.1 | 0.1 | 0.1 | |
| glycine | | 1.0 | 1.0 | 1.0 | 1.0 | 1.0 | |
| arginine | | adjusting to pH 8 | | | | | |
| water | | the balance | the balance | the balance | the balance | the balance | |
| total | | 100 | 100 | 100 | 100 | 100 | |
| Evaluation | dyeing properties | Δ | ○ | ○ | ○ | ⊙ | Δ |
| | shampoo-fastness after 1st run | Δ | ○ | ○ | ○ | ○ | Δ |
| | after 3rd run | Δ ~ X | ○ | ○ | ○ | ○ | X |
| | after 8th run | X | ○ | ○ | ○ | ○ | X |
| | after 10th run | X | Δ | Δ | Δ | ○ | X |

TABLE 1

In the above Table 1, only the invention product 4 was heat-treated (at 60° C. for 15 minutes).

The formulation of the control product 2 was as follows:
benzyl alcohol: 5.0
ethanol (95%): 10.0
propylene glycol: 10.0
purple No. 410: 0.1
black No. 401: 0.1
citric acid: adjusting to pH 4
water: the balance
total (%): 100.

EXAMPLE 2

To a styling gel base composition comprising the following components (1) to (7) were added dyes Basic Red 76 (C.I. 12251) and Basic Brown 16 (C.I. (12550), N-acetylcysteine, benzyl alcohol and diethylene glycol ethyl ether. The styling gel composition (the hair dye composition of the present invention) of the following formulation thus obtained was used to dye the hair to thereby gives results which will be described below.

| (1) 2-hexyldecyltrimethylammonium chloride | 0.5% |
|---|---|
| (2) polyether-modified silicone of general formula [IV] (wherein s = 25, t = 4, u = 10, v = 0, and A = OH) | 1.0% |
| (3) cationized cellulose (polymer JR-400) | 2.0% |
| (4) hydroxyethylcellulose | 0.5% |
| (5) polyoxyethylene oleyl ether (EO = 5) | 0.3% |
| (6) perfume | 0.15% |
| (7) water | balance |
| (8) Basic Red 76 | 0.05% |
| (9) Basic Brown 16 | 0.05% |
| (10) N-acetylcysteine | 0.1% |
| (11) benzyl alcohol | 5.0% |
| (12) diethylene glycol ethyl ether | 5.0% |
| | 100.0% |

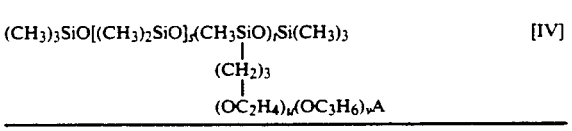

Dyeing method and results

The above styling gel composition was applied to a golden hair wig (base color: medium blonde). As a result, the wig was dyed into vivid red (mahogany red) uniformly.

The shampoo-fastness was evaluated by the following method.

A half (right) of the above-mentioned dyed wig was shampooed once every three days. After one, two, three and four weeks, the color of the shampooed half was compared with another half (left) to evaluate the extent of the decoloring with the naked eye. Table 2 shows the results.

TABLE 2

| | Right half (shampooed) | Left half (control) |
|---|---|---|
| after 1 week | ⊙ | standard |
| after 2 weeks | ⊙ | " |
| after 3 weeks | ⊙ | " |
| after 4 weeks | ○ | " |

Criteria of evaluation

⊙: the same as the left half as the control (vivid red color remaining).
○: almost the same as the control (vivid red color remaining).
△: decolored compared with the control.
·: seriously decolored compared with the control.

EXAMPLE 3

To a styling mousse base composition comprising the following components (1) to (8) were added dyes Black No. 401, Purple No. 401, Orange No. 205 and Green No. 401, N-acetylcysteine, benzyl alcohol and diethylene glycol ethyl ether. The styling mousse composition (the hair dye composition of the present invention) of the following formulation thus obtained was used to dye the hair in the following manner to thereby give results which will be described below.

| | |
|---|---|
| (1) 2-dodecylhexadecyltrimethylammonium chloride | 0.5% |
| (2) methylphenylpolysiloxane of general formula [V] (wherein a = 0, b = 50, and c = 0) | 1.0% |
| (3) polyether-modified silicone of general formula [IV] (wherein s = 60, t = 5, u = 15, v = 30, and A = OCH₃) | 1.5% |
| (4) Plysize L53P (a product of GOOU Kagaku) | 8.0% |
| (5) polyoxyethylene hexadecyl ether (EO = 10) | 0.5% |
| (6) ethanol | 5.0% |
| (7) perfume | 0.2% |
| (8) water | the balance |
| (9) N-acetylcysteine | 0.2% |
| (10) benzyl alcohol | 5.0% |
| (11) diethylene glycol ethyl ether | 5.0% |
| (12) Black No. 401 | 0.01% |
| (13) Purple No. 401 | 0.01% |
| (14) Orange No. 205 | 0.005% |
| (15) Green No. 401 | 0.005% |
| (16) LPG (4.0 kg/cm²G, 20° C.) | 10.0% |
| | 100.0% |

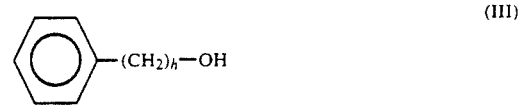

Dyeing method and results

The above-mentioned styling mousse composition was applied to the hair of a male white-haired panelist. As a result, the white hair was dyed dark brown and thus became inconspicuous.

After a half month, the fastness was evaluated with the naked eye to reveal that the white hair was still inconspicuous, suggesting a high fastness.

What is claimed is:

1. A hair dye composition comprising the following three components (A), (B) and (C):

(A) 0.5 to 5.0% by weight of one or more of a cysteine derivative represented by the following general formula (I):

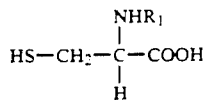

wherein $R_1$ represents a hydrogen atom or an acyl or alkyl group having one to three carbon atoms, and glutathione, or a salt thereof;

(B) 0.1 to 50% by weight of an aromatic alcohol and/or a compound represented by the following general formula (II):

$$R_2\text{—OCH}_2\text{CH}_2\text{OCH}_2\text{CH}_2\text{OH} \qquad (II)$$

wherein $R_2$ represents an alkyl group having one to five carbon atoms; and (C) 0.0001 to 20% by weight of a direct dye.

2. The hair dye composition as claimed in claim 1, wherein said cysteine derivative is selected from the group consisting of N-acetyl-3-mercaptoalanine, N-propyl-3-mercaptoalanine, N-ethyl-3-mercaptoalanine and glutathione.

3. The hair dye composition as claimed in claim 1, wherein said cysteine derivative salt is selected from the group consisting of salts of an inorganic acid and salts of an organic acid.

4. A hair dye composition as claimed in claim 1, wherein said aromatic alcohol as the component (B) is a phenyl monoalkyl alcohol represented by the following general formula (III):

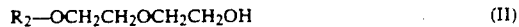

wherein h is a number of from 1 to 5.

5. A hair dye composition as claimed in claim 1, wherein the compound represented by the general formula (II) as the component (B) is selected from among diethylene glycol methyl ether, diethylene glycol ethyl ether, diethylene diglycol propyl ether, diethylene glycol butyl ether and diethylene glycol pentyl ether.

6. The hair dye composition as claimed in claim 1, wherein the pH value thereof is adjusted to 6 to 10.

7. The hair dye composition as claimed in claim 3, wherein said inorganic acid is hydrochloric acid, sulfuric acid or nitric acid.

8. The hair dye composition as claimed in claim 3, wherein said organic acid is acetic acid, formic acid, oxalic acid and citric acid.

9. The hair dye composition as claimed in claim 1, wherein said direct dye is a non-polymeric dye.

10. The hair dye composition as claimed in claim 9, wherein said non-polymeric dye is a nitrogenous benzene derivative, an indoamine dye, a diaryl dye, a xanthine dye, a triarylmethane dye, an azine dye, an acridine dye, or an anthraquinone dye.

* * * * *